United States Patent
Lyman et al.

(10) Patent No.: US 7,045,128 B2
(45) Date of Patent: May 16, 2006

(54) ANTIBODIES AGAINST FLT3-LIGAND

(75) Inventors: Stewart D. Lyman, Seattle, WA (US); M. Patricia Beckmann, Poulsbo, WA (US)

(73) Assignee: Immunex Corporation, Seattle, WA (US)

( * ) Notice: Subject to any disclaimer, the term of this patent is extended or adjusted under 35 U.S.C. 154(b) by 273 days.

(21) Appl. No.: 10/095,449

(22) Filed: Mar. 13, 2002

(65) Prior Publication Data

US 2002/0160004 A1 Oct. 31, 2002

Related U.S. Application Data

(60) Division of application No. 08/669,692, filed on Jun. 24, 1996, now Pat. No. 6,630,143, which is a continuation-in-part of application No. 08/444,632, filed on May 19, 1995, now abandoned, which is a division of application No. 08/243,545, filed on May 11, 1994, now Pat. No. 5,554,512, which is a continuation-in-part of application No. 08/209,502, filed on Mar. 7, 1994, now abandoned, which is a continuation-in-part of application No. 08/162,407, filed on Dec. 3, 1993, now abandoned, which is a continuation-in-part of application No. 08/111,758, filed on Aug. 25, 1993, now abandoned, which is a continuation-in-part of application No. 08/106,463, filed on Aug. 12, 1993, now abandoned, and a continuation-in-part of application No. 08/068,394, filed on May 24, 1993, now abandoned.

(51) Int. Cl.
*A61K 39/395* (2006.01)
*C07K 16/28* (2006.01)
*C12N 15/13* (2006.01)
*C12N 15/63* (2006.01)

(52) U.S. Cl. .............. 424/153.1; 424/130.1; 424/139.1; 424/141.1; 424/143.1; 424/144.1; 424/173.1; 435/252.3; 435/252.33; 435/320.1; 530/387.1; 530/387.9; 530/388.1; 530/388.2; 530/388.22; 530/388.7; 530/388.73; 530/389.1; 530/389.6; 536/23.1; 536/23.5

(58) Field of Classification Search ............. 424/130.1, 424/139.1, 141.1, 153.1, 143.1, 173.1, 144.1; 530/387.1, 388.2, 388.73, 350, 387.9, 388.1, 530/388.22, 388.7, 389.1, 389.6; 536/23.1, 536/23.5; 435/252.3, 320.1, 252.33
See application file for complete search history.

(56) References Cited

U.S. PATENT DOCUMENTS 5,185,438 A 2/1993 Lemischka
6,630,143 B1 * 10/2003 Lyman et al. ............ 424/153.1

FOREIGN PATENT DOCUMENTS

WO WO 94 26891 11/1994

OTHER PUBLICATIONS

Lyman et al, *Cell*, 75:1157-1167 (1993).
Rosnet et al, *Oncogene*, 6:1641-1650 (1991).
Lyman et al, *Oncogene*, 8(4):815-822 (1993).
Lyman et al, *Blood*, 83(10):2795-2801 (1994).

* cited by examiner

*Primary Examiner*—Phillip Gambel
(74) *Attorney, Agent, or Firm*—Sughrue Mion, PLLC

(57) ABSTRACT

Ligands for flt3 receptors capable of transducing self-renewal signals to regulate the growth, proliferation or differentiation of progenitor cells and stem cells are disclosed. The invention is directed to anti-flt3-L antibodies and enzyme-linked immunosorbent assays comprising such antibodies.

15 Claims, No Drawings

SEQUENCE LISTING (1) GENERAL INFORMATION:

(iii) NUMBER OF SEQUENCES: 8

(2) INFORMATION FOR SEQ ID NO: 1:

(i) SEQUENCE CHARACTERISTICS:
      (A) LENGTH: 879 base pairs
      (B) TYPE: nucleic acid
      (C) STRANDEDNESS: single
      (D) TOPOLOGY: linear (ii) MOLECULE TYPE: cDNA to mRNA (iii) HYPOTHETICAL: NO (iv) ANTI-SENSE: NO (ix) FEATURE:
      (A) NAME/KEY: misc_feature
      (B) LOCATION: 1..25

(ix) FEATURE:
      (A) NAME/KEY: misc_feature
      (B) LOCATION: 855..879

(ix) FEATURE:
      (A) NAME/KEY: CDS
      (B) LOCATION: 57..752

(xi) SEQUENCE DESCRIPTION: SEQ ID NO: 1:

```
GTCGACTGGA ACGAGACGAC CTGCTCTGTC ACAGGCATGA GGGGTCCCCG GCAGAG            56

ATG ACA GTG CTG GCG CCA GCC TGG AGC CCA AAT TCC TCC CTG TTG CTG         104
Met Thr Val Leu Ala Pro Ala Trp Ser Pro Asn Ser Ser Leu Leu Leu
 1               5                  10                  15

CTG TTG CTG CTG CTG AGT CCT TGC CTG CGG GGG ACA CCT GAC TGT TAC         152
Leu Leu Leu Leu Leu Ser Pro Cys Leu Arg Gly Thr Pro Asp Cys Tyr
                 20                  25                  30

TTC AGC CAC AGT CCC ATC TCC TCC AAC TTC AAA GTG AAG TTT AGA GAG         200
Phe Ser His Ser Pro Ile Ser Ser Asn Phe Lys Val Lys Phe Arg Glu
             35                  40                  45

TTG ACT GAC CAC CTG CTT AAA GAT TAC CCA GTC ACT GTG GCC GTC AAT         248
Leu Thr Asp His Leu Leu Lys Asp Tyr Pro Val Thr Val Ala Val Asn
 50                  55                  60

CTT CAG GAC GAG AAG CAC TGC AAG GCC TTG TGG AGC CTC TTC CTA GCC         296
Leu Gln Asp Glu Lys His Cys Lys Ala Leu Trp Ser Leu Phe Leu Ala
65                  70                  75                  80

CAG CGC TGG ATA GAG CAA CTG AAG ACT GTG GCA GGG TCT AAG ATG CAA         344
Gln Arg Trp Ile Glu Gln Leu Lys Thr Val Ala Gly Ser Lys Met Gln
                 85                  90                  95

ACG CTT CTG GAG GAC GTC AAC ACC GAG ATA CAT TTT GTC ACC TCA TGT         392
Thr Leu Leu Glu Asp Val Asn Thr Glu Ile His Phe Val Thr Ser Cys
                100                 105                 110

ACC TTC CAG CCC CTA CCA GAA TGT CTG CGA TTC GTC CAG ACC AAC ATC         440
Thr Phe Gln Pro Leu Pro Glu Cys Leu Arg Phe Val Gln Thr Asn Ile
            115                 120                 125

TCC CAC CTC CTG AAG GAC ACC TGC ACA CAG CTG CTT GCT CTG AAG CCC         488
Ser His Leu Leu Lys Asp Thr Cys Thr Gln Leu Leu Ala Leu Lys Pro
        130                 135                 140

TGT ATC GGG AAG GCC TGC CAG AAT TTC TCT CGG TGC CTG GAG GTG CAG         536
Cys Ile Gly Lys Ala Cys Gln Asn Phe Ser Arg Cys Leu Glu Val Gln
145                 150                 155                 160

TGC CAG CCG GAC TCC TCC ACC CTG CTG CCC CCA AGG AGT CCC ATA GCC         584
```

```
Cys Gln Pro Asp Ser Ser Thr Leu Leu Pro Pro Arg Ser Pro Ile Ala
            165                 170                 175

CTA GAA GCC ACG GAG CTC CCA GAG CCT CGG CCC AGG CAG CTG TTG CTC     632
Leu Glu Ala Thr Glu Leu Pro Glu Pro Arg Pro Arg Gln Leu Leu Leu
            180                 185                 190

CTG CTG CTG CTG CTG CCT CTC ACA CTG GTG CTG CTG GCA GCC GCC TGG     680
Leu Leu Leu Leu Leu Pro Leu Thr Leu Val Leu Leu Ala Ala Ala Trp
        195                 200                 205

GGC CTT CGC TGG CAA AGG GCA AGA AGG AGG GGG GAG CTC CAC CCT GGG     728
Gly Leu Arg Trp Gln Arg Ala Arg Arg Arg Gly Glu Leu His Pro Gly
    210                 215                 220

GTG CCC CTC CCC TCC CAT CCC TAGGATTCGA GCCTTGTGCA TCGTTGACTC        779
Val Pro Leu Pro Ser His Pro
225             230

AGCCAGGGTC TTATCTCGGT TACACCTGTA ATCTCAGCCC TTGGGAGCCC AGAGCAGGAT   839

TGCTGAATGG TCTGGAGCAG GTCGTCTCGT TCCAGTCGAC                         879

(2) INFORMATION FOR SEQ ID NO: 2:

(i) SEQUENCE CHARACTERISTICS:
        (A) LENGTH: 231 amino acids
        (B) TYPE: amino acid
        (D) TOPOLOGY: linear (ii) MOLECULE TYPE: protein (xi) SEQUENCE DESCRIPTION: SEQ ID NO: 2:

Met Thr Val Leu Ala Pro Ala Trp Ser Pro Asn Ser Ser Leu Leu Leu
1               5                   10                  15

Leu Leu Leu Leu Leu Ser Pro Cys Leu Arg Gly Thr Pro Asp Cys Tyr
            20                  25                  30

Phe Ser His Ser Pro Ile Ser Ser Asn Phe Lys Val Lys Phe Arg Glu
        35                  40                  45

Leu Thr Asp His Leu Leu Lys Asp Tyr Pro Val Thr Val Ala Val Asn
    50                  55                  60

Leu Gln Asp Glu Lys His Cys Lys Ala Leu Trp Ser Leu Phe Leu Ala
65                  70                  75                  80

Gln Arg Trp Ile Glu Gln Leu Lys Thr Val Ala Gly Ser Lys Met Gln
                85                  90                  95

Thr Leu Leu Glu Asp Val Asn Thr Glu Ile His Phe Val Thr Ser Cys
            100                 105                 110

Thr Phe Gln Pro Leu Pro Glu Cys Leu Arg Phe Val Gln Thr Asn Ile
        115                 120                 125

Ser His Leu Leu Lys Asp Thr Cys Thr Gln Leu Leu Ala Leu Lys Pro
    130                 135                 140

Cys Ile Gly Lys Ala Cys Gln Asn Phe Ser Arg Cys Leu Glu Val Gln
145                 150                 155                 160

Cys Gln Pro Asp Ser Ser Thr Leu Leu Pro Pro Arg Ser Pro Ile Ala
            165                 170                 175

Leu Glu Ala Thr Glu Leu Pro Glu Pro Arg Pro Arg Gln Leu Leu Leu
            180                 185                 190

Leu Leu Leu Leu Leu Pro Leu Thr Leu Val Leu Leu Ala Ala Ala Trp
        195                 200                 205

Gly Leu Arg Trp Gln Arg Ala Arg Arg Arg Gly Glu Leu His Pro Gly
    210                 215                 220

Val Pro Leu Pro Ser His Pro
225             230
```

(2) INFORMATION FOR SEQ ID NO: 3:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (iii) HYPOTHETICAL: NO (iv) ANTI-SENSE: NO (xi) SEQUENCE DESCRIPTION: SEQ ID NO: 3:

```
TCGACTGGAA CGAGACGACC TGCT                                      24
```

(2) INFORMATION FOR SEQ ID NO: 4:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (iii) HYPOTHETICAL: NO (iv) ANTI-SENSE: NO (xi) SEQUENCE DESCRIPTION: SEQ ID NO: 4:

```
AGCAGGTCGT CTCGTTCCAG                                           20
```

(2) INFORMATION FOR SEQ ID NO: 5:

(i) SEQUENCE CHARACTERISTICS:
        (A) LENGTH: 988 base pairs
        (B) TYPE: nucleic acid
        (C) STRANDEDNESS: single
        (D) TOPOLOGY: linear (ii) MOLECULE TYPE: cDNA to mRNA (iii) HYPOTHETICAL: NO (iv) ANTI-SENSE: NO (ix) FEATURE:
        (A) NAME/KEY: CDS
        (B) LOCATION: 30..734

(xi) SEQUENCE DESCRIPTION: SEQ ID NO: 5:

```
CGGCCGGAAT TCCGGGGCCC CCGGCCGAA ATG ACA GTG CTG GCG CCA GCC TGG        53
                                 Met Thr Val Leu Ala Pro Ala Trp
                                  1               5

AGC CCA ACA ACC TAT CTC CTC CTG CTG CTG CTG AGC TCG GGA CTC           101
Ser Pro Thr Thr Tyr Leu Leu Leu Leu Leu Leu Ser Ser Gly Leu
 10                  15                  20

AGT GGG ACC CAG GAC TGC TCC TTC CAA CAC AGC CCC ATC TCC TCC GAC       149
Ser Gly Thr Gln Asp Cys Ser Phe Gln His Ser Pro Ile Ser Ser Asp
     25                  30                  35              40

TTC GCT GTC AAA ATC CGT GAG CTG TCT GAC TAC CTG CTT CAA GAT TAC       197
Phe Ala Val Lys Ile Arg Glu Leu Ser Asp Tyr Leu Leu Gln Asp Tyr
                 45                  50                  55

CCA GTC ACC GTG GCC TCC AAC CTG CAG GAC GAG GAG CTC TGC GGG GGC       245
Pro Val Thr Val Ala Ser Asn Leu Gln Asp Glu Glu Leu Cys Gly Gly
             60                  65                  70

CTC TGG CGG CTG GTC CTG GCA CAG CGC TGG ATG GAG CGG CTC AAG ACT       293
Leu Trp Arg Leu Val Leu Ala Gln Arg Trp Met Glu Arg Leu Lys Thr
         75                  80                  85
```

```
GTC GCT GGG TCC AAG ATG CAA GGC TTG CTG GAG CGC GTG AAC ACG GAG          341
Val Ala Gly Ser Lys Met Gln Gly Leu Leu Glu Arg Val Asn Thr Glu
        90                  95                 100

ATA CAC TTT GTC ACC AAA TGT GCC TTT CAG CCC CCC CCC AGC TGT CTT          389
Ile His Phe Val Thr Lys Cys Ala Phe Gln Pro Pro Pro Ser Cys Leu
105                 110                 115                 120

CGC TTC GTC CAG ACC AAC ATC TCC CGC CTC CTG CAG GAG ACC TCC GAG          437
Arg Phe Val Gln Thr Asn Ile Ser Arg Leu Leu Gln Glu Thr Ser Glu
                125                 130                 135

CAG CTG GTG GCG CTG AAG CCC TGG ATC ACT CGC CAG AAC TTC TCC CGG          485
Gln Leu Val Ala Leu Lys Pro Trp Ile Thr Arg Gln Asn Phe Ser Arg
            140                 145                 150

TGC CTG GAG CTG CAG TGT CAG CCC GAC TCC TCA ACC CTG CCA CCC CCA          533
Cys Leu Glu Leu Gln Cys Gln Pro Asp Ser Ser Thr Leu Pro Pro Pro
        155                 160                 165

TGG AGT CCC CGG CCC CTG GAG GCC ACA GCC CCG ACA GCC CCG CAG CCC          581
Trp Ser Pro Arg Pro Leu Glu Ala Thr Ala Pro Thr Ala Pro Gln Pro
    170                 175                 180

CCT CTG CTC CTC CTA CTG CTG CTG CCC GTG GGC CTC CTG CTG CTG GCC          629
Pro Leu Leu Leu Leu Leu Leu Leu Pro Val Gly Leu Leu Leu Leu Ala
185                 190                 195                 200

GCT GCC TGG TGC CTG CAC TGG CAG AGG ACG CGG CGG AGG ACA CCC CGC          677
Ala Ala Trp Cys Leu His Trp Gln Arg Thr Arg Arg Arg Thr Pro Arg
                205                 210                 215

CCT GGG GAG CAG GTG CCC CCC GTC CCC AGT CCC CAG GAC CTG CTG CTT          725
Pro Gly Glu Gln Val Pro Pro Val Pro Ser Pro Gln Asp Leu Leu Leu
            220                 225                 230

GTG GAG CAC TGACCTGGCC AAGGCCTCAT CCTGCGGAGC CTTAAACAAC                  774
Val Glu His
        235

GCAGTGAGAC AGACATCTAT CATCCCATTT TACAGGGGAG GATACTGAGG CACACAGAGG        834

GGAGTCACCA GCCAGAGGAT GTATAGCCTG GACACAGAGG AAGTTGGCTA GAGGCCGGTC        894

CCTTCCTTGG GCCCCTCTCA TTCCCTCCCC AGAATGGAGG CAACGCCAGA ATCCAGCACC        954

GGCCCCATTT ACCCAACTCT GAACAAAGCC CCCG                                    988

(2) INFORMATION FOR SEQ ID NO: 6:

(i) SEQUENCE CHARACTERISTICS:
        (A) LENGTH: 235 amino acids
        (B) TYPE: amino acid
        (D) TOPOLOGY: linear (ii) MOLECULE TYPE: protein (xi) SEQUENCE DESCRIPTION: SEQ ID NO: 6:

Met Thr Val Leu Ala Pro Ala Trp Ser Pro Thr Thr Tyr Leu Leu Leu
  1               5                  10                  15

Leu Leu Leu Ser Ser Gly Leu Ser Gly Thr Gln Asp Cys Ser Phe
              20                  25                  30

Gln His Ser Pro Ile Ser Ser Asp Phe Ala Val Lys Ile Arg Glu Leu
            35                  40                  45

Ser Asp Tyr Leu Leu Gln Asp Tyr Pro Val Thr Val Ala Ser Asn Leu
        50                  55                  60

Gln Asp Glu Glu Leu Cys Gly Gly Leu Trp Arg Leu Val Leu Ala Gln
 65                 70                  75                  80

Arg Trp Met Glu Arg Leu Lys Thr Val Ala Gly Ser Lys Met Gln Gly
                85                  90                  95
```

-continued

```
Leu Leu Glu Arg Val Asn Thr Glu Ile His Phe Val Thr Lys Cys Ala
            100                 105                 110
Phe Gln Pro Pro Pro Ser Cys Leu Arg Phe Val Gln Thr Asn Ile Ser
        115                 120                 125
Arg Leu Leu Gln Glu Thr Ser Glu Gln Leu Val Ala Leu Lys Pro Trp
    130                 135                 140
Ile Thr Arg Gln Asn Phe Ser Arg Cys Leu Glu Leu Gln Cys Gln Pro
145                 150                 155                 160
Asp Ser Ser Thr Leu Pro Pro Trp Ser Pro Arg Pro Leu Glu Ala
                165             170                 175
Thr Ala Pro Thr Ala Pro Gln Pro Pro Leu Leu Leu Leu Leu Leu Leu
            180                 185                 190
Pro Val Gly Leu Leu Leu Ala Ala Ala Trp Cys Leu His Trp Gln
        195                 200                 205
Arg Thr Arg Arg Arg Thr Pro Arg Pro Gly Glu Gln Val Pro Pro Val
    210                 215                 220
Pro Ser Pro Gln Asp Leu Leu Leu Val Glu His
225                 230                 235
```

(2) INFORMATION FOR SEQ ID NO: 7:

(i) SEQUENCE CHARACTERISTICS:
      (A) LENGTH: 71 base pairs
      (B) TYPE: nucleic acid
      (C) STRANDEDNESS: single
      (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO: 7:

```
AATTGGTACC TTTGGATAAA AGAGACTACA AGGACGACGA TGACAAGACA CCTGACTGTT        60

ACTTCAGCCA C                                                            71
```

(2) INFORMATION FOR SEQ ID NO: 8:

(i) SEQUENCE CHARACTERISTICS:
      (A) LENGTH: 37 base pairs
      (B) TYPE: nucleic acid
      (C) STRANDEDNESS: single
      (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO: 8:

```
ATATGGATCC CTACTGCCTG GGCCGAGGCT CTGGGAG                                 37
```

ANTIBODIES AGAINST FLT3-LIGAND

CROSS-REFERENCE TO RELATED APPLICATIONS

This Application is a Divisional of U.S. application Ser. No. 08/669,692, filed Jun. 24, 1996 now U.S. Pat. No. 6,630,143; which in turn is a Continuation-In-Part of U.S. application Ser. No. 08/444,632, filed May 19, 1995 (now abandoned); which in turn is a Divisional of U.S. application Ser. No. 08/243,545, filed May 11, 1994 (now U.S. Pat. No. 5,554,512); which in turn is a Continuation-In-Part of U.S. application Ser. No. 08/209,502, filed Mar. 7, 1994 (now abandoned); which in turn is a Continuation-In-Part of U.S. application Ser. No. 08/162,407, Dec. 3, 1993 (now abandoned); which in turn is a Continuation-In-Part of U.S. application Ser. No. 08/111,758, filed Aug. 25, 1993 (now abandoned); which in turn is a Continuation-In-Part of U.S. application Ser. No. 08/106,463, filed Aug. 12, 1993 (now abandoned); which in turn is a Continuation-In-Part of U.S. application Ser. No. 08/068,394, filed May 24, 1993 (now abandoned).

FIELD OF THE INVENTION

The present invention relates to antibodies, and in particular, monoclonal antibodes, against mammalian flt3-ligands and kits incorporating the antibodies.

BACKGROUND OF THE INVENTION

Blood cells originate from hematopoietic stem cells that become committed to differentiate along certain lineages, i.e., erythroid, megakaryocytic, granulocytic, monocytic, and lymphocytic. Cytokines that stimulate the proliferation and maturation of cell precursors are called colony stimulating factors ("CSFs"). Several CSFs are produced by T-lymphocytes, including interleukin-3 ("IL-3"), granulocyte-monocyte CSF (GM-CSF), granulocyte CSF (G-CSF), and monocyte CSF (M-CSF). These CSFs affect both mature cells and stem cells. Heretofore no factors have been discovered that are able to predominantly affect stem cells.

Tyrosine kinase receptors ("TKRs") are growth factor receptors that regulate the proliferation and differentiation of a number of cells (Yarden, Y. & Ullrich, A. *Annu. Rev. Biochem.*, 57, 443–478, 1988; and Cadena, D. L. & Gill, G. N. *FASEB J.*, 6, 2332–2337, 1992). Certain TKRs function within the hematopoietic system. For example, signaling through the colony-stimulating factor type 1 ("CSF-1"), receptor c-fms regulates the survival, growth and differentiation of monocytes (Stanley et al., *J. Cell Biochem.*, 21, 151–159, 1983). Steel factor ("SF", also known as mast cell growth factor, stem cell factor or kit ligand), acting through c-kit, stimulates the proliferation of cells in both myeloid and lymphoid compartments.

Flt3 (Rosnet et al. *Oncogene*, 6, 1641–1650, 1991) and flk-2 (Matthews et al., *Cell*, 65, 1143–1152, 1991) are variant forms of a TKR that is related to the c-fms and c-kit receptors. The flk-2 gene product is expressed on hematopoietic and progenitor cells, while the flt3 gene product has a more general tissue distribution. The flt3 and flk-2 receptor proteins are similar in amino acid sequence and vary at two amino acid residues in the extracellular domain and diverge in a 31 amino acid segment located near the C-termini (Lyman et al., *Oncogene*, 8, 815–822, 1993).

Flt3-ligand ("flt3-L") has been found to regulate the growth and differentiation of progenitor and stem cells and is likely to possess clinical utility in treating hematopoietic disorders, in particular, aplastic anemia and myelodysplastic syndromes. Additionally, flt3-L will be useful in allogeneic, syngeneic or autologous bone marrow transplants in patients undergoing cytoreductive therapies, as well as cell expansion. Flt3-L will also be useful in gene therapy and progenitor and stem cell mobilization systems.

Cancer is treated with cytoreductive therapies that involve administration of ionizing radiation or chemical toxins that kill rapidly dividing cells. Side effects typically result from cytotoxic effects upon normal cells and can limit the use of cytoreductive therapies. A frequent side effect is myelosuppression, or damage to bone marrow cells that give rise to white and red blood cells and platelets. As a result of myelosuppression, patients develop cytopenia, or blood cell deficits, that increase risk of infection and bleeding disorders.

Cytopenias increase morbidity, mortality, and lead to under-dosing in cancer treatment. Many clinical investigators have manipulated cytoreductive therapy dosing regimens and schedules to increase dosing for cancer therapy, while limiting damage to bone marrow. One approach involves bone marrow or peripheral blood cell transplants in which bone marrow or circulating hematopoietic progenitor or stem cells are removed before cytoreductive therapy and then reinfused following therapy to restore hematopoietic function. U.S. Pat. No. 5,199,942, incorporated herein by reference, describes a method for using GM-CSF, IL-3, SF, GM-CSF/IL-3 fusion proteins, erythropoietin ("EPO") and combinations thereof in autologous transplantation regimens.

High-dose chemotherapy is therapeutically beneficial because it can produce an increased frequency of objective response in patients with metastatic cancers, particularly breast cancer, when compared to standard dose therapy. This can result in extended disease-free remission for some even poor-prognosis patients. Nevertheless, high-dose chemotherapy is toxic and many resulting clinical complications are related to infections, bleeding disorders and other effects associated with prolonged periods of myelosuppression.

Myelodysplastic syndromes are acquired stem cell disorders characterized by impaired cellular maturation, progressive pancytopenia, and functional abnormalities of mature cells. They have also been characterized by variable degrees of cytopenia, ineffective erythropoiesis and myelopoiesis with bone marrow cells that are normal or increased in number and that have peculiar morphology. Bennett et. al. (*Br. J. Haematol.* 1982; 51:189–199) divided these disorders into five subtypes: refractory anemia, refractory anemia with ringed sideroblasts, refractory anemia with excess blasts, refractory anemia with excess blasts in transformation, and chronic myelomonocytic leukemia. Although a significant percentage of these patients develop acute leukemia, a majority die from infectious or hemorrhagic complications. Treatment of theses syndromes with retinoids, vitamin D, and cytarabine has not been successful. Most of the patients suffering from these syndromes are elderly and are not suitable candidates for bone marrow transplantation or aggressive antileukemic chemotherapy.

Aplastic anemia is another acquired disease entity that is characterized by bone marrow failure and severe pancytopenia. Unlike myelodysplastic syndrome, the bone marrow is acellular or hypocellular in this disorder. Current treatments include bone marrow transplantation from a histocompatible donor or immunosuppressive treatment with antithymocyte globulin (ATG). Similarly to myelodysplastic syndrome, most patients suffering from this syndrome are elderly and are unsuitable for bone marrow transplantation or for aggressive antileukemic chemotherapy. Mortality in these patients is exceedingly high from infectious or hemorrhagic complications.

Another hematopoietic disorder involving multiple blood lineages includes Fanconi's anemia (a congenital deficiency of red cells, white cells and platelets). Plycythenias are diseases characterized by the overproduction of red cells, white cells and platelets.

SUMMARY OF THE INVENTION

The present invention pertains to antibodies, and in particular monoclonal antibodies, that are immunoreactive with flt3-L. Also included in the invention are ELISA kits utilizing such antibodies, and to methods of determining the serum concentration of flt3-L in a patient.

It has recently been determined that flt3-L serum levels are elevated in patients suffering from Fanconi's anemia, acquired aplastic anemia, myelodysplastic syndromes such as refractory anemia. Use of the antibodies would determine flt3-L serum levels and possibly be predictive of the status of the disease.

DETAILED DESCRIPTION OF THE INVENTION

A cDNA encoding murine flt3-L has been isolated and is disclosed in SEQ ID NO:1. A cDNA encoding human flt3-L also has been isolated and is disclosed in SEQ ID NO:5. This discovery of cDNAs encoding murine and human flt3-L enables construction of expression vectors comprising cDNAs encoding flt3-L; host cells transfected or transformed with the expression vectors; biologically active murine and human flt3-L as homogeneous proteins; and antibodies immunoreactive with the murine and the human flt3-L.

As used herein, the term "flt3-L" refers to a genus of polypeptides that bind and complex independently with flt3 receptor found on progenitor and stem cells. The term "flt3-L" encompasses proteins having the amino acid sequence 1 to 231 of SEQ ID NO:2 or the amino acid sequence 1 to 235 of SEQ ID NO:6, as well as those proteins having a high degree of similarity or a high degree of identity with the amino acid sequence 1 to 231 of SEQ ID NO:2 or the amino acid sequence 1 to 235 of SEQ ID NO:6, and which proteins are biologically active and bind the flt3 receptor. In addition, the term refers to biologically active gene products of the DNA of SEQ ID NO:1 or SEQ ID NO:5. Further encompassed by the term "flt3-L" are the membrane-bound proteins (which include an intracellular region, a membrane region, and an extracellular region), and soluble or truncated proteins which comprise primarily the extracellular portion of the protein, retain biological activity and are capable of being secreted. Specific examples of such soluble proteins are those comprising the sequence of amino acids 28–163 of SEQ ID NO:2 and amino acids 28–160 of SEQ ID NO:6.

The term "biologically active" as it refers to flt3-L, means that the flt3-L is capable of binding to flt3. Alternatively, "biologically active" means the flt3-L is capable of transducing a stimulatory signal to the cell through the membrane-bound flt3.

"Isolated" means that flt3-L is free of association with other proteins or polypeptides, for example, as a purification product of recombinant host cell culture or as a purified extract.

A "flt3-L variant" as referred to herein, means a polypeptide substantially homologous to native flt3-L, but which has an amino acid sequence different from that of native flt3-L (human, murine or other mammalian species) because of one or more deletions, insertions or substitutions. The variant amino acid sequence preferably is at least 80% identical to a native flt3-L amino acid sequence, most preferably at least 90% identical. The percent identity may be determined, for example, by comparing sequence information using the GAP computer program, version 6.0 described by Devereux et al. (*Nucl. Acids Res.* 12:387, 1984) and available from the University of Wisconsin Genetics Computer Group (UWGCG). The GAP program utilizes the alignment method of Needleman and Wunsch (*J. Mol. Biol.* 48:443, 1970), as revised by Smith and Waterman (*Adv. Appl. Math* 2:482, 1981). The preferred default parameters for the GAP program include: (1) a unary comparison matrix (containing a value of 1 for identities and 0 for non-identities) for nucleotides, and the weighted comparison matrix of Gribskov and Burgess, *Nucl. Acids Res.* 14:6745, 1986, as described by Schwartz and Dayhoff, eds., *Atlas of Protein Sequence and Structure*, National Biomedical Research Foundation, pp. 353–358, 1979; (2) a penalty of 3.0 for each gap and an additional 0.10 penalty for each symbol in each gap; and (3) no penalty for end gaps. Variants may comprise conservatively substituted sequences, meaning that a given amino acid residue is replaced by a residue having similar physiochemical characteristics. Examples of conservative substitutions include substitution of one aliphatic residue for another, such as Ile, Val, Leu, or Ala for one another, or substitutions of one polar residue for another, such as between Lys and Arg; Glu and Asp; or Gln and Asn. Other such conservative substitutions, for example, substitutions of entire regions having similar hydrophobicity characteristics, are well known. Naturally occurring flt3-L variants are also encompassed by the invention. Examples of such variants are proteins that result from alternate mRNA splicing events or from proteolytic cleavage of the flt3-L protein, wherein the flt3-L binding property is retained. Alternate splicing of mRNA may yield a truncated but biologically active flt3-L protein, such as a naturally occurring soluble form of the protein, for example. Variations attributable to proteolysis include, for example, differences in the N- or C-termini upon expression in different types of host cells, due to proteolytic removal of one or more terminal amino acids from the flt3-L protein (generally from 1–5 terminal amino acids).

As described supra., an aspect of the invention is soluble flt3-L polypeptides. Soluble flt3-L polypeptides comprise all or part of the extracellular domain of a native flt3-L but lack the transmembrane region that would cause retention of the polypeptide on a cell membrane. Soluble flt3-L polypeptides advantageously comprise the native (or a heterologous) signal peptide when initially synthesized to promote secretion, but the signal peptide is cleaved upon secretion of flt3-L from the cell. Soluble flt3-L polypeptides encompassed by the invention retain the ability to bind the flt3 receptor. Indeed, soluble flt3-L may also include part of the transmembrane region or part of the cytoplasmic domain or other sequences, provided that the soluble flt3-L protein can be secreted.

Soluble flt3-L may be identified (and distinguished from its non-soluble membrane-bound counterparts) by separating intact cells which express the desired protein from the culture medium, e.g., by centrifugation, and assaying the medium (supernatant) for the presence of the desired protein. The presence of flt3-L in the medium indicates that the protein was secreted from the cells and thus is a soluble form of the desired protein.

Soluble forms of flt3-L possess many advantages over the native bound flt3-L protein. Purification of the proteins from recombinant host cells is feasible, since the soluble proteins are secreted from the cells. Further, soluble proteins are generally more suitable for intravenous administration.

Examples of soluble flt3-L polypeptides include those comprising a substantial portion of the extracellular domain of a native flt3-L protein. Such soluble mammalian flt3-L proteins comprise amino acids 28 through 188 of SEQ ID NO:2 or amino acids 28 through 182 of SEQ ID NO:6. In addition, truncated soluble flt3-L proteins comprising less than the entire extracellular domain are included in the invention. Such truncated soluble proteins are represented by the sequence of amino acids 28–163 of SEQ ID NO:2, and amino acids 28–160 of SEQ ID NO:6. When initially expressed within a host cell, soluble flt3-L may additionally comprise one of the heterologous signal peptides described below that is functional within the host cells employed. Alternatively, the protein may comprise the native signal peptide, such that the mammalian flt3-L comprises amino acids 1 through 188 of SEQ ID NO:2 or amino acids 1 through 182 of SEQ ID NO:6. In one embodiment of the invention, soluble flt3-L was expressed as a fusion protein comprising (from N- to C-terminus) the yeast α factor signal peptide, a FLAG® peptide described below and in U.S. Pat. No. 5,011,912, and soluble flt3-L consisting of amino acids 28 to 188 of SEQ ID NO:2. This recombinant fusion protein is expressed in and secreted from yeast cells. The FLAG® peptide facilitates purification of the protein, and subsequently may be cleaved from the soluble flt3-L using bovine mucosal enterokinase. Isolated DNA sequences encoding soluble flt3-L proteins are encompassed by the invention.

Truncated flt3-L, including soluble polypeptides, may be prepared by any of a number of conventional techniques. A desired DNA sequence may be chemically synthesized using techniques known per se. DNA fragments also may be produced by restriction endonuclease digestion of a full length cloned DNA sequence, and isolated by electrophoresis on agarose gels. Linkers containing restriction endonuclease cleavage site(s) may be employed to insert the desired DNA fragment into an expression vector, or the fragment may be digested at cleavage sites naturally present therein. The well known polymerase chain reaction procedure also may be employed to amplify a DNA sequence encoding a desired protein fragment. As a further alternative, known mutagenesis techniques may be employed to insert a stop codon at a desired point, e.g., immediately downstream of the codon for the last amino acid of the extracellular domain.

In another approach, enzymatic treatment (e.g., using Bal 31 exonuclease) may be employed to delete terminal nucleotides from a DNA fragment to obtain a fragment having a particular desired terminus. Among the commercially available linkers are those that can be ligated to the blunt ends produced by Bal 31 digestion, and which contain restriction endonuclease cleavage site(s). Alternatively, oligonucleotides that reconstruct the N- or C-terminus of a DNA fragment to a desired point may be synthesized and ligated to the DNA fragment. The synthesized oligonucleotide may contain a restriction endonuclease cleavage site upstream of the desired coding sequence and position an initiation codon (ATG) at the N-terminus of the coding sequence.

As stated above, the invention provides isolated or homogeneous flt3-L polypeptides, both recombinant and non-recombinant Variants and derivatives of native flt3-L proteins that retain the desired biological activity (e.g., the ability to bind flt3) may be obtained by mutations of nucleotide sequences coding for native flt3-L polypeptides. Alterations of the native amino acid sequence may be accomplished by any of a number of conventional methods. Mutations can be introduced at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion.

Alternatively, oligonucleotide-directed site-specific mutagenesis procedures can be employed to provide an altered gene wherein predetermined codons can be altered by substitution, deletion or insertion. Exemplary methods of making the alterations set forth above are disclosed by Walder et al. (*Gene* 42:133, 1986); Bauer et al. (*Gene* 37:73, 1985); Craik (*BioTechniques*, January 1985, 12–19); Smith et al. (*Genetic Engineering: Principles and Methods*, Plenum Press, 1981); Kunkel (*Proc. Natl. Acad. Sci. USA* 82:488, 1985); Kunkel et al. (*Methods in Enzymol.* 154:367, 1987); and U.S. Pat. Nos. 4,518,584 and 4,737,462 all of which are incorporated by reference.

Flt3-L may be modified to create flt3-L derivatives by forming covalent or aggregative conjugates with other chemical moieties, such as glycosyl groups, lipids, phosphate, acetyl groups and the like. Covalent derivatives of flt3-L may be prepared by linking the chemical moieties to functional groups on flt3-L amino acid side chains or at the N-terminus or C-terminus of a flt3-L polypeptide or the extracellular domain thereof. Other derivatives of flt3-L within the scope of this invention include covalent or aggregative conjugates of flt3-L or its fragments with other proteins or polypeptides, such as by synthesis in recombinant culture as N-terminal or C-terminal fusions. For example, the conjugate may comprise a signal or leader polypeptide sequence (e.g. the α-factor leader of *Saccharomyces*) at the N-terminus of a flt3-L polypeptide. The signal or leader peptide co-translationally or post-translationally directs transfer of the conjugate from its site of synthesis to a site inside or outside of the cell membrane or cell wall.

Flt3-L polypeptide fusions can comprise peptides added to facilitate purification and identification of flt3-L. Such peptides include, for example, poly-His or the antigenic identification peptides described in U.S. Pat. No. 5,011,912 and in Hopp et al., *Bio/Technology* 6:1204, 1988.

The invention further includes flt3-L polypeptides with or without associated native-pattern glycosylation. Flt3-L expressed in yeast or mammalian expression systems (e.g., COS-7 cells) may be similar to or significantly different from a native flt3-L polypeptide in molecular weight and glycosylation pattern, depending upon the choice of expression system. Expression of flt3-L polypeptides in bacterial expression systems, such as *E. coli*, provides non-glycosylated molecules.

Equivalent DNA constructs that encode various additions or substitutions of amino acid residues or sequences, or deletions of terminal or internal residues or sequences not needed for biological activity or binding are encompassed by the invention. For example, N-glycosylation sites in the flt3-L extracellular domain can be modified to preclude glycosylation, allowing expression of a reduced carbohydrate analog in mammalian and yeast expression systems. N-glycosylation sites in eukaryotic polypeptides are characterized by an amino acid triplet Asn-X-Y, wherein X is any amino acid except Pro and Y is Ser or Thr. The murine and human flt3-L proteins each comprise two such triplets, at amino acids 127–129 and 152–154 of SEQ ID NO:2, and at amino acids 126–128 and 150–152 of SEQ ID NO:6, respectively. Appropriate substitutions, additions or deletions to the nucleotide sequence encoding these triplets will result in prevention of attachment of carbohydrate residues at the Asn side chain. Alteration of a single nucleotide, chosen so that Asn is replaced by a different amino acid, for example, is sufficient to inactivate an N-glycosylation site. Known procedures for inactivating N-glycosylation sites in proteins include those described in U.S. Pat. No. 5,071,972 and EP 276,846, hereby incorporated by reference.

In another example, sequences encoding Cys residues that are not essential for biological activity can be altered to cause the Cys residues to be deleted or replaced with other amino acids, preventing formation of incorrect intramolecular disulfide bridges upon renaturation. Other equivalents are prepared by modification of adjacent dibasic amino acid residues to enhance expression in yeast systems in which KEX2 protease activity is present. EP 212,914 discloses the use of site-specific mutagenesis to inactivate KEX2 protease processing sites in a protein. KEX2 protease processing sites are inactivated by deleting, adding or substituting residues to alter Arg-Arg, Arg-Lys, and Lys-Arg pairs to eliminate the occurrence of these adjacent basic residues. Lys-Lys pairings are considerably less susceptible to KEX2 cleavage, and conversion of Arg-Lys or Lys-Arg to Lys-Lys represents a conservative and preferred approach to inactivating KEX2 sites. Both murine and human flt3-L contain two KEX2 protease processing sites at amino acids 216–217 and 217–218 of SEQ ID NO:2 and at amino acids 211–212 and 212–213 of SEQ ID NO:6, respectively.

Nucleic acid sequences within the scope of the invention include isolated DNA and RNA sequences that hybridize to the native flt3-L nucleotide sequences disclosed herein under conditions of moderate or severe stringency, and which encode biologically active flt3-L. Conditions of moderate stringency, as defined by Sambrook et al. *Molecular Cloning: A Laboratory Manual*, 2 ed. Vol. 1, pp. 1.101–104, Cold Spring Harbor Laboratory Press, (1989), include use of a prewashing solution of 5×SSC, 0.5% SDS, 1.0 mM EDTA (pH 8.0) and hybridization conditions of about 55° C., 5×SSC, overnight. Conditions of severe stringency include higher temperatures of hybridization and washing. The skilled artisan will recognize that the temperature and wash solution salt concentration may be adjusted as necessary according to factors such as the length of the probe.

Due to the known degeneracy of the genetic code wherein more than one codon can encode the same amino acid, a DNA sequence may vary from that shown in SEQ ID NO:1 and SEQ ID NO:5 and still encode an flt3-L protein having the amino acid sequence of SEQ ID NO:2 and SEQ ID NO:6, respectively. Such variant DNA sequences may result from silent mutations (e.g., occurring during PCR amplification), or may be the product of deliberate mutagenesis of a native sequence.

The invention provides equivalent isolated DNA sequences encoding biologically active flt3-L, selected from: (a) DNA derived from the coding region of a native mammalian flt3-L gene; (b) cDNA comprising the nucleotide sequence presented in SEQ ID NO:1 or SEQ ID NO:5; (c) DNA capable of hybridization to a DNA of (a) under moderately stringent conditions and which encodes biologically active flt3-L; and (d) DNA which is degenerate as a result of the genetic code to a DNA defined in (a), (b) or (c) and which encodes biologically active flt3-L. Flt3-L proteins encoded by such DNA equivalent sequences are encompassed by the invention.

DNA that are equivalents to the DNA sequence of SEQ ID NO:1 or SEQ ID NO:5, will hybridize under moderately stringent conditions to the native DNA sequence that encode polypeptides comprising amino acid sequences of 28–163 of SEQ ID NO:2 or 28–160 of SEQ ID NO:6. Examples of flt3-L proteins encoded by such DNA, include, but are not limited to, flt3-L fragments (soluble or membrane-bound) and flt3-L proteins comprising inactivated N-glycosylation site(s), inactivated KEX2 protease processing site(s), or conservative amino acid substitution(s), as described above. Flt3-L proteins encoded by DNA derived from other mammalian species, wherein the DNA will hybridize to the cDNA of SEQ ID NO:1 or SEQ ID NO:5, are also encompassed.

Variants possessing the requisite ability to bind flt3 receptor may be identified by any suitable assay. Biological activity of flt3-L may be determined, for example, by competition for binding to the ligand binding domain of flt3 receptor (i.e. competitive binding assays).

One type of a competitive binding assay for a flt3-L polypeptide uses a radiolabeled, soluble human flt3-L and intact cells expressing cell surface flt3 receptors. Instead of intact cells, one could substitute soluble flt3 receptors (such as a flt3:Fc fusion protein) bound to a solid phase through the interaction of a Protein A, Protein G or an antibody to the flt3 or Fc portions of the molecule, with the Fc region of the fusion protein. Another type of competitive binding assay utilizes radiolabeled soluble flt3 receptors such as a flt3:Fc fusion protein, and intact cells expressing flt3-L. Alternatively, soluble flt3-L could be bound to a solid phase to positively select flt3 expressing cells.

Competitive binding assays can be performed following conventional methodology. For example, radiolabeled flt3-L can be used to compete with a putative flt3-L homolog to assay for binding activity against surface-bound flt3 receptors. Qualitative results can be obtained by competitive autoradiographic plate binding assays, or Scatchard plots may be utilized to generate quantitative results.

Alternatively, flt3-binding proteins, such as flt3-L and anti-flt3 antibodies, can be bound to a solid phase such as a column chromatography matrix or a similar substrate suitable for identifying, separating or purifying cells that express the flt3 receptor on their surface. Binding of flt3-binding proteins to a solid phase contacting surface can be accomplished by any means, for example, by constructing a flt3-L:Fc fusion protein and binding such to the solid phase through the interaction of Protein A or Protein G. Various other means for fixing proteins to a solid phase are well known in the art and are suitable for use in the present invention. For example, magnetic microspheres can be coated with flt3-binding proteins and held in the incubation vessel through a magnetic field. Suspensions of cell mixtures containing hematopoietic progenitor or stem cells are contacted with the solid phase that has flt3-binding proteins thereon. Cells having the flt3 receptor on their surface bind to the fixed flt3-binding protein and unbound cells then are washed away. This affinity-binding method is useful for purifying, screening or separating such flt3-expressing cells from solution. Methods of releasing positively selected cells from the solid phase are known in the art and encompass, for example, the use of enzymes. Such enzymes are preferably non-toxic and non-injurious to the cells and are preferably directed to cleaving the cell-surface binding partner. In the case of flt3:flt3-L interactions, the enzyme preferably would cleave the flt3 receptor, thereby freeing the resulting cell suspension from the "foreign" flt3-L material. The purified cell population then may be expanded ex vivo prior to transplantation to a patient in an amount sufficient to reconstitute the patient's hematopoietic and immune system.

Alternatively, mixtures of cells suspected of containing flt3+ cells first can be incubated with a biotinylated flt3-binding protein. Incubation periods are typically at least one hour in duration to ensure sufficient binding to flt3. The resulting mixture then is passed through a column packed with avidin-coated beads, whereby the high affinity of biotin for avidin provides the binding of the cell to the beads. Use of avidin-coated beads is known in the art. See Berenson, et al. *J. Cell. Biochem.*, 10D:239 (1986). Wash of unbound material and the release of the bound cells is performed using conventional methods.

In the methods described above, suitable flt3-binding proteins are flt3-L, anti-flt3 antibodies, and other proteins that are capable of high-affinity binding of flt3. A preferred flt3-binding protein is flt3-L.

As described above, flt3-L of the invention can be used to separate cells expressing flt3 receptors. In an alternative method, flt3-L or an extracellular domain or a fragment thereof can be conjugated to a detectable moiety such as $^{125}$I to detect flt3 expressing cells. Radiolabeling with $^{125}$I can be performed by any of several standard methodologies that yield a functional $^{125}$I-flt3-L molecule labeled to high specific activity. Or an iodinated or biotinylated antibody against the flt3 region or the Fc region of the molecule could be used. Another detectable moiety such as an enzyme that can catalyze a colorimetric or fluorometric reaction, biotin or avidin may be used. Cells to be tested for flt3 receptor expression can be contacted with labeled flt3-L. After incubation, unbound labeled flt3-L is removed and binding is measured using the detectable moiety.

The binding characteristics of flt3-L (including variants) may also be determined using the conjugated, soluble flt3 receptors (for example, $^{125}$I-flt3:Fc) in competition assays similar to those described above. In this case, however, intact cells expressing flt3 receptors, or soluble flt3 receptors bound to a solid substrate, are used to measure the extent to which a sample containing a putative flt3-L variant competes for binding with a conjugated a soluble flt3 to flt3-L.

Other means of assaying for flt3-L include the use of anti-flt3-L antibodies, cell lines that proliferate in response to flt3-L, or recombinant cell lines that express flt3 receptor and proliferate in the presence of flt3-L. For example, the BAF/BO3 cell line lacks the flt3 receptor and is IL-3 dependent. (See Hatakeyama, et al., *Cell*, 59: 837–845 (1989)). BAF/BO3 cells transfected with an expression vector comprising the flt3 receptor gene proliferate in response to either IL-3 or flt3-L. An example of a suitable expression vector for transfection of flt3 is the pCAV/NOT plasmid, see Mosley et al., *Cell*, 59: 335–348 (1989).

Flt3-L polypeptides may exist as oligomers, such as covalently-linked or non-covalently-linked dimers or trimers. Oligomers may be linked by disulfide bonds formed between cysteine residues on different flt3-L polypeptides. In one embodiment of the invention, a flt3-L dimer is created by fusing flt3-L to the Fc region of an antibody (e.g., IgG1) in a manner that does not interfere with binding of flt3-L to the flt3-ligand-binding domain. The Fc polypeptide preferably is fused to the C-terminus of a soluble flt3-L (comprising only the extracellular domain). General preparation of fusion proteins comprising heterologous polypeptides fused to various portions of antibody-derived polypeptides (including the Fc domain) has been described, e.g., by Ashkenazi et al. (*PNAS USA* 88:10535, 1991) and Byrn et al. (*Nature* 344:677, 1990), hereby incorporated by reference. A gene fusion encoding the flt3-L:Fc fusion protein is inserted into an appropriate expression vector. Flt3-L:Fc fusion proteins are allowed to assemble much like antibody molecules, whereupon interchain disulfide bonds form between Fc polypeptides, yielding divalent flt3-L. If fusion proteins are made with both heavy and light chains of an antibody, it is possible to form a flt3-L oligomer with as many as four flt3-L extracellular regions. Alternatively, one can link two soluble flt3-L domains with a peptide linker.

Recombinant expression vectors containing a DNA encoding flt3-L can be prepared using well known methods. The expression vectors include a flt3-L DNA sequence operably linked to suitable transcriptional or translational regulatory nucleotide sequences, such as those derived from a mammalian, microbial, viral, or insect gene. Examples of regulatory sequences include transcriptional promoters, operators, or enhancers, an mRNA ribosomal binding site, and appropriate sequences which control transcription and translation initiation and termination. Nucleotide sequences are "operably linked" when the regulatory sequence functionally relates to the flt3-L DNA sequence. Thus, a promoter nucleotide sequence is operably linked to a flt3-L DNA sequence if the promoter nucleotide sequence controls the transcription of the flt3-L DNA sequence. The ability to replicate in the desired host cells, usually conferred by an origin of replication, and a selection gene by which transformants are identified, may additionally be incorporated into the expression vector.

In addition, sequences encoding appropriate signal peptides that are not naturally associated with flt3-L can be incorporated into expression vectors. For example, a DNA sequence for a signal peptide (secretory leader) may be fused in-frame to the flt3-L sequence so that flt3-L is initially translated as a fusion protein comprising the signal peptide. A signal peptide that is functional in the intended host cells enhances extracellular secretion of the flt3-L polypeptide. The signal peptide may be cleaved from the flt3-L polypeptide upon secretion of flt3-L from the cell.

Suitable host cells for expression of flt3-L polypeptides include prokaryotes, yeast or higher eukaryotic cells. Appropriate cloning and expression vectors for use with bacterial, fungal, yeast, and mammalian cellular hosts are described, for example, in Pouwels et al. *Cloning Vectors: A Laboratory Manual*, Elsevier, N.Y., (1985). Cell-free translation systems could also be employed to produce flt3-L polypeptides using RNAs derived from DNA constructs disclosed herein.

Prokaryotes include gram negative or gram positive organisms, for example, *E. coli* or *Bacilli*. Suitable prokaryotic host cells for transformation include, for example, *E. coli, Bacillus subtilis, Salmonella typhimurium*, and various other species within the genera *Pseudomonas, Streptomyces*, and *Staphylococcus*. In a prokaryotic host cell, such as *E. coli*, a flt3-L polypeptide may include an N-terminal methionine residue to facilitate expression of the recombinant polypeptide in the prokaryotic host cell. The N-terminal Met may be cleaved from the expressed recombinant flt3-L polypeptide.

Expression vectors for use in prokaryotic host cells generally comprise one or more phenotypic selectable marker genes. A phenotypic selectable marker gene is, for example, a gene encoding a protein that confers antibiotic resistance or that supplies an autotrophic requirement. Examples of useful expression vectors for prokaryotic host cells include those derived from commercially available plasmids such as the cloning vector pBR322 (ATCC 37017). pBR322 contains genes for ampicillin and tetracycline resistance and thus provides simple means for identifying transformed cells. To construct en expression vector using pBR322, an appropriate promoter and a flt3-L DNA sequence are inserted into the pBR322 vector. Other commercially available vectors include, for example, pKK223-3 (Pharmacia Fine Chemicals, Uppsala, Sweden) and PGEM1 (Promega Biotec, Madison, Wis., USA).

Promoter sequences commonly used for recombinant prokaryotic host cell expression vectors include β-lactamase (penicillinase), lactose promoter system (Chang et al., *Nature* 275:615, 1978; and Goeddel et al., *Nature* 281:544, 1979), tryptophan (trp) promoter system (Goeddel et al., *Nucl. Acids Res.* 8:4057, 1980; and EP-A-36776) and tac promoter (Maniatis, *Molecular Cloning: A Laboratory Manual*, Cold Spring Harbor Laboratory, p. 412, 1982). A particularly useful prokaryotic host cell expression system employs a phage λ $P_L$ promoter and a cI857ts thermolabile repressor sequence. Plasmid vectors available from the American Type Culture Collection which incorporate derivatives of the λ $P_L$ promoter include plasmid pHUB2 (resident in *E. coli* strain JMB9 (ATCC 37092)) and pPLc28 (resident in *E. coli* RR1 (ATCC 53082)).

Flt3-L polypeptides alternatively may be expressed in yeast host cells, preferably from the *Saccharomyces* genus (e.g., *S. cerevisiae*). Other genera of yeast, such as *Pichia, K. lactis* or *Kluyveromyces*, may also be employed. Yeast vectors will often contain an origin of replication sequence from a 2μ yeast plasmid, an autonomously replicating sequence (ARS), a promoter region, sequences for polyadenylation, sequences for transcription termination, and a selectable marker gene. Suitable promoter sequences for yeast vectors include, among others, promoters for metallothionein, 3-phosphoglycerate kinase (Hitzeman et al., *J. Biol. Chem.* 255:2073, 1980) or other glycolytic enzymes (Hess et al., *J. Adv. Enzyme Reg.* 7:149, 1968; and Holland et al., *Biochem.* 17:4900, 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Other suitable vectors and promoters for use in yeast expression are further described in Hitzeman, EPA-73,657 or in Fleer et. al., *Gene*, 107:285–195 (1991); and van den Berg et. al., *Bio/Technology,* 8:135–139 (1990). Another alternative is the glucose-repressible ADH2 promoter described by Russell et al. (*J. Biol. Chem.* 258:2674, 1982) and Beier et al. (*Nature* 300:724, 1982). Shuttle vectors replicable in both yeast and *E. coli* may be constructed by inserting DNA sequences from pBR322 for selection and replication in *E. coli* (Amp$^r$ gene and origin of replication) into the above-described yeast vectors.

The yeast α-factor leader sequence may be employed to direct secretion of the flt3-L polypeptide. The α-factor leader sequence is often inserted between the promoter sequence and the structural gene sequence. See, e.g., Kurjan et al., *Cell* 30:933, 1982; Bitter et al., *Proc. Natl. Acad. Sci. USA* 81:5330, 1984; U.S. Pat. No. 4,546,082; and EP 324,274. Other leader sequences suitable for facilitating secretion of recombinant polypeptides from yeast hosts are known to those of skill in the art. A leader sequence may be modified near its 3' end to contain one or more restriction sites. This will facilitate fusion of the leader sequence to the structural gene.

Yeast transformation protocols are known to those of skill in the art. One such protocol is described by Hinnen et al., *Proc. Natl. Acad. Sci. USA* 75:1929, 1978. The Hinnen et al. protocol selects for Trp$^+$ transformants in a selective medium, wherein the selective medium consists of 0.67% yeast nitrogen base, 0.5% casamino acids, 2% glucose, 10 μg/ml adenine and 20 μg/ml uracil.

Yeast host cells transformed by vectors containing ADH2 promoter sequence may be grown for inducing expression in a "rich" medium. An example of a rich medium is one consisting of 1% yeast extract, 2% peptone, and 1% glucose supplemented with 80 μg/ml adenine and 80 μg/ml uracil. Derepression of the ADH2 promoter occurs when glucose is exhausted from the medium.

Mammalian or insect host cell culture systems could also be employed to express recombinant flt3-L polypeptides. Baculovirus systems for production of heterologous proteins in insect cells are reviewed by Luckow and Summers, *Bio/Technology* 6:47 (1988). Established cell lines of mammalian origin also may be employed. Examples of suitable mammalian host cell lines include the COS-7 line of monkey kidney cells (ATCC CRL 1651) (Gluzman et al., *Cell* 23:175, 1981), L cells, C127 cells, 3T3 cells (ATCC CCL 163), Chinese hamster ovary (CHO) cells, HeLa cells, and BHK (ATCC CRL 10) cell lines, and the CV-1/EBNA-1 cell line derived from the African green monkey kidney cell line CVI (ATCC CCL 70) as described by McMahan et al. (*EMBO J.* 10: 2821, 1991).

Transcriptional and translational control sequences for mammalian host cell expression vectors may be excised from viral genomes. Commonly used promoter sequences and enhancer sequences are derived from Polyoma virus, Adenovirus 2, Simian Virus 40 (SV40), and human cytomegalovirus. DNA sequences derived from the SV40 viral genome, for example, SV40 origin, early and late promoter, enhancer, splice, and polyadenylation sites may be used to provide other genetic elements for expression of a structural gene sequence in a mammalian host cell. Viral early and late promoters are particularly useful because both are easily obtained from a viral genome as a fragment which may also contain a viral origin of replication (Fiers et al., *Nature* 273:113, 1978). Smaller or larger SV40 fragments may also be used, provided the approximately 250 bp sequence extending from the Hind III site toward the Bgl I site located in the SV40 viral origin of replication site is included.

Exemplary expression vectors for use in mammalian host cells can be constructed as disclosed by Okayama and Berg (*Mol. Cell. Biol.* 3:280, 1983). A useful system for stable high level expression of mammalian cDNAs in C127 murine mammary epithelial cells can be constructed substantially as described by Cosman et al. (*Mol. Immunol.* 23:935, 1986). A useful high expression vector, PMLSV N1/N4, described by Cosman et al., *Nature* 312:768, 1984 has been deposited as ATCC 39890. Additional useful mammalian expression vectors are described in EP-A-0367566, and in U.S. patent application Ser. No. 07/701,415, filed May 16, 1991, incorporated by reference herein. The vectors may be derived from retroviruses. In place of the native signal sequence, a heterologous signal sequence may be added, such as the signal sequence for IL-7 described in U.S. Pat. No. 4,965, 195; the signal sequence for IL-2 receptor described in Cosman et al., *Nature* 312:768 (1984); the IL-4 signal peptide described in EP 367,566; the type I IL-1 receptor signal peptide described in U.S. Pat. No. 4,968,607; and the type II IL-1 receptor signal peptide described in EP 460,846.

Flt3-L as an isolated or homogeneous protein according to the invention may be produced by recombinant expression systems as described above or purified from naturally occurring cells. Flt3-L can be purified to substantial homogeneity, as indicated by a single protein band upon analysis by SDS-polyacrylamide gel electrophoresis (SDS-PAGE).

One process for producing flt3-L comprises culturing a host cell transformed with an expression vector comprising a DNA sequence that encodes flt3-L under conditions sufficient to promote expression of flt3-L. Flt3-L is then recovered from culture medium or cell extracts, depending upon the expression system employed. As is known to the skilled artisan, procedures for purifying a recombinant protein will vary according to such factors as the type of host cells employed and whether or not the recombinant protein is secreted into the culture medium.

For example, when expression systems that secrete the recombinant protein are employed, the culture medium first may be concentrated using a commercially available protein concentration filter, for example, an Amicon or Millipore Pellicon ultrafiltration unit. Following the concentration step, the concentrate can be applied to a purification matrix such as a gel filtration medium. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. Sulfopropyl groups are preferred. Finally, one or more reversed-phase high performance liquid chromatography (RP-HPLC) steps employing hydrophobic RP-HPLC media, (e.g., silica gel having pendant methyl or other aliphatic groups) can be employed to further purify flt3-L. Some or all of the foregoing purification steps, in various combinations, are well known and can be employed to provide a substantially homogeneous recombinant protein.

It is possible to utilize an affinity column comprising the ligand binding domain of flt3 receptors to affinity-purify expressed flt3-L polypeptides. Flt3-L polypeptides can be removed from an affinity column using conventional techniques, e.g., in a high salt elution buffer and then dialyzed into a lower salt buffer for use or by changing pH or other components depending on the affinity matrix utilized. Alternatively, the affinity column may comprise an antibody that binds flt3-L. Example 6 describes a procedure for employing flt3-L of the invention to generate monoclonal antibodies directed against flt3-L.

Recombinant protein produced in bacterial culture is usually isolated by initial disruption of the host cells, centrifugation, extraction from cell pellets if an insoluble polypeptide, or from the supernatant fluid if a soluble polypeptide, followed by one or more concentration, salting-out, ion exchange, affinity purification or size exclusion chromatography steps. Finally, RP-HPLC can be employed for final purification steps. Microbial cells can be disrupted by any convenient method, including freeze-thaw cycling, sonication, mechanical disruption, or use of cell lysing agents.

Transformed yeast host cells are preferably employed to express flt3-L as a secreted polypeptide in order to simplify purification. Secreted recombinant polypeptide from a yeast host cell fermentation can be purified by methods analogous to those disclosed by Urdal et al. (*J. Chromatog.* 296:171, 1984). Urdal et al. describe two sequential, reversed-phase HPLC steps for purification of recombinant human IL-2 on a preparative HPLC column.

Antibodies can be generated against flt3-L using conventional procedures, such as that described in Example 6, below. The antibodies are useful in a sensitive enzyme linked immunosorbent assay (ELISA) used to measure the concentration of flt3-L in plasma or serum. Indeed, concentrations of flt3-L in plasma or serum from normal individuals are quite low, with 88% of normal individuals (53 of 60) having flt3-L levels below 100 pg/ml. In contrast, the majority of patients with anemias affecting multiple hematopoietic lineages, e.g., Fanconi's anemia or acquired aplstic anemia, had highly elevated plasma or serum levels of flt3-L (up to 10,000 pg/ml). Flt3-L levels in anemias affecting predominantly erythroid lineage, e.g., Diamond Blackfan anemia, or pure red cell aplasia, were not elevated. Levels of flt3-L were found to be normal in patients having HIV, AML, ALL or rheumatoid arthritis. Thus, levels of flt3-L in serum or plasma may be indicative of disease status.

Because flt3-L may be used to mobilize stem or progenitor cells to the peripheral blood, it is possible that the flt3-L ELISA could be used to determine whether a patient is a good candidate for mobilization with flt3-L. A high concentration of serum or plasma flt3-L might be an indication that administration of exogenous flt3-L would result in less stem cell or progenitor cell mobilization, than in a patient having a low serum or plasma level of flt3-L.

The ELISA of the invention encompasses the steps comprising adsorbing the anti-flt3-L antibody onto to a substrate, incubating the substrate and antibody with the samples to be measured, after washing to remove unbound flt3-L, a polyclonal antibody against flt3-L is added followed by washing to remove unbound polyclonal anti-flt3-L. A labelled antibody against the anti-flt3-L polyclonal antibody is added and incubated with the complex. Unbound labelled antibody is then removed. The amount of labelled antibody is quantified and compared to a control thereby indicating the quantity of flt3-L in the sample.

In addition to the above, the following examples are provided to illustrate particular embodiments and not to limit the scope of the invention.

EXAMPLE 1

Preparation of Flt3-Receptor:Fc Fusion Protein

This example describes the cloning of murine flt3 cDNA, and the construction of an expression vector encoding a soluble murine flt3-receptor:Fc fusion protein for use in detecting cDNA clones encoding flt3-L. Polymerase chain reaction (PCR) cloning of the flt3 cDNA from a murine T-cell was accomplished using the oligonucleotide primers and the methods as described by Lyman et al., *Oncogene*, 8:815–822, (1993), incorporated herein by reference. The cDNA sequence and encoded amino acid sequence for mouse flt3 receptor is presented by Rosnet et el., *Oncogene*, 6:1641–1650, (1991), hereby incorporated by reference. The mouse flt3 protein has a 542 amino acid extracellular domain, a 21 amino acid transmembrane domain, and a 437 amino acid cytoplasmic domain.

Prior to fusing the murine flt3 cDNA to the N-terminus of cDNA encoding the Fc portion of a human IgG1 molecule, the amplified mouse flt3 cDNA fragment was inserted into Asp718-NotI site of pCAV/NOT, described in PCT Application WO 90/05183. DNA encoding a single chain polypeptide comprising the Fc region of a human IgG1 antibody was cloned into the SpeI site of the pBLUE-SCRIPT SK® vector, which is commercially available from Stratagene Cloning Systems, La Jolla, Calif. This plasmid vector is replicable in *E. coli* and contains a polylinker segment that includes 21 unique restriction sites. A unique BglII site was introduced near the 5' end of the inserted Fc encoding sequence, such that the BglII site encompasses the codons for amino acids three and four of the Fc polypeptide.

The encoded Fc polypeptide extends from the N-terminal hinge region to the native C-terminus, i.e., is an essentially full-length antibody Fc region. Fragments of Fc regions, e.g., those that are truncated at the C-terminal end, also may be employed. The fragments preferably contain multiple cysteine residues (at least the cysteine residues in the hinge reaction) to permit interchain disulfide bonds to form between the Fc polypeptide portions of two separate flt3:Fc fusion proteins, forming dimers as discussed above.

An Asp718 restriction endonuclease cleavage site was introduced upstream of the flt3 coding region. An Asp 718-NotI fragment of mouse flt3 cDNA (comprising the entire extracellular domain, the transmembrane region, and a small portion of the cytoplasmic domain) was isolated. The above-described Asp718-NotI flt3 partial cDNA was cloned into the pBLUESCRIPT SK® vector containing the Fc cDNA, such that the flt3 cDNA is positioned upstream of the Fc cDNA. Single stranded DNA derived from the resulting gene fusion was mutagenized by the method described in Kunkel (*Proc. Natl. Acad. Sci. USA* 82:488, 1985) and Kunkel et al. (*Methods in Enzymol.* 154:367, 1987) in order to perfectly fuse the entire extracellular domain of flt3 to the Fc sequence. The mutagenized DNA was sequenced to confirm that the proper nucleotides had been removed (i.e., transmembrane region and partial cytoplasmic domain DNA was deleted) and that the flt3 and Fc sequences were in the same reading frame. The fusion cDNA was then excised and inserted into a mammalian expression vector designated sfHAV-EO 409 which was cut with SalI-NotI, and the SalI and Asp718 ends blunted. The sfHAV-EO vector (also known as pDC406) is described by McMahan et al. (*EMBO J.*, 10; No. 10:2821–2832 (1991)).

Flt3:Fc fusion proteins preferably are synthesized in recombinant mammalian cell culture. The flt3:Fc fusion-containing expression vector was transfected into CV-1 cells (ATCC CCL 70) and COS-7 cells (ATCC CRL 1651), both derived from monkey kidney. Flt3:Fc expression level was relatively low in both CV-1 and COS-7 cells. Thus, expression in 293 cells (transformed primary human embryonal kidney cells, ATCC CRL 1573) was attempted.

The 293 cells transfected with the sfHAV-EO/flt3:Fc vector were cultivated in roller bottles to allow transient expression of the fusion protein, which is secreted into the culture medium via the flt3 signal peptide. The fusion protein was purified on protein A Sepharose columns, eluted, and used to screen cells for the ability to bind flt3:Fc, as described in Examples 2 and 3.

EXAMPLE 2

Screening Cells for Flt3:Fc Binding

Approximately 100 different primary cells and cell lines falling into the following general categories: primary murine fetal brain cells, murine fetal liver cell lines, rat fetal brain cell lines, human lung carcinoma (fibroblastoid) cell lines, human and murine lymphoid and myeloid cell lines were assayed for flt3:Fc binding. Cell lines were incubated with flt3:Fc, followed by a biotinylated anti-human Fc antibody, followed by streptavidin-phycoerythrin (Becton Dickinson). The biotinylated antibody was purchased from Jackson Immunoresearch Laboratories. Streptavidin binds to the biotin molecule attached to the anti-human Fc antibody, which in turn binds to the Fc portion of the flt3:Fc fusion protein. Phycoerythrin is a fluorescent phycobiliprotein which serves as a detectable label. The level of fluorescence signal was measured for each cell type using a FACScan® flow cytometer (Becton Dickinson). The cell types deemed positive for flt3:Fc binding were identified.

EXAMPLE 3

Isolation and Cloning of Flt3 L cDNA from Murine T-Cell cDNA Library

A murine T-cell cDNA library of cell line P7B-0.3A4 was chosen as a possible source of flt3-L cDNA. P7B-0.3A4 is a murine T cell clone that is Thy1.2$^+$, CD4$^-$, CD8$^-$, TCRab$^\pm$, CD44$^+$. It was originally cloned at a cell density of 0.33 cells/well in the presence of rHuIL-7 and immobilized anti-CD3 MAb, and was grown in continuous culture for more than 1 year by passage once a week in medium containing 15 ng/ml rHuIL-7. The parent cell line was derived from lymph node cells of SJL/J mice immunized with 50 nmoles PLP$_{139-151}$ peptide and 100 μg *Mycobacterium tuberculosis* H37Ra in Incomplete Freund's Adjuvant. PLP is the proteolipid protein component of the myelin sheath of the central nervous system. The peptide composed of amino acids 139–151 has previously been shown to be the encephalogenic peptide in experimental autoimmune encephalomyelitis (EAE), a murine model for multiple sclerosis in SJL/J mice. (Touhy, V. K., Z. Lu, R. A. Sobel, R. A. Laursen and M. B. Lees; 1989. Identification of an encephalitogenic determinant of myelin proteolipid protein for SJL mice. *J. Immunol.* 142:1523.) After the initial culture in the presence of antigen, the parent cell line, designated PLP7, had been in continuous culture with rHuIL-7 (and without antigen) for more than 6 months prior to cloning.

P7B-0.3A4 proliferates only in response to very high concentrations of PLP$_{139-151}$ peptide in the presence of irradiated syngeneic splenocytes and is not encephalogenic or alloresponsive. This clone proliferates in response to immobilized anti-CD3 MAb, IL-2, and IL-7, but not IL-4.

Binding of flt3:Fc was observed on murine T-cells and human T-cells, and therefore a murine T-cell line was chosen (0.3A4) due to its ease of growth. A murine 0.3A4 cDNA library in sfHAV-EO was prepared as described in McMahan et al. (*EMBO J.*, 10; No:10; 2821–2832 1991). sfHAV-EO is a mammalian expression vector that also replicates in *E. coli*. sfHAV-EO contains origins of replication derived from SV40, Epstein-Barr virus and pBR322 and is a derivative of HAV-EO described by Dower et al., *J. Immunol.* 142:4314 (1989). sfHAV-EO differs from HAV-EO by the deletion of the intron present in the adenovirus 2 tripartite leader sequence in HAV-EO. Briefly, murine T-cell cDNA was cloned into the SalI site of sfHAV-EO by an adaptor method similar to that described by Haymerle et al (*Nucl. Acids Res.* 14:8615, 1986), using the following oligonucleotide adapter pair:

```
5' TCGACTGGAACGAGACGACCTGCT 3'      SEQ ID NO:3

3'      GACCTTGCTCTGCTGGACGA 5'     SEQ ID NO:4
```

Double-stranded, blunt-ended, random-primed cDNA was prepared from 0.3A4 poly (A)+ RNA essentially as described by Gubler and Hoffman, *Gene*, 25:263–269 (1983), using a Pharmacia DNA kit. The above adapters were added to the cDNA as described by Haymerle et al. Low molecular weight material was removed by passage over Sephacryl S-1000 at 65° C., and the cDNA was ligated into sfHAV-EO410, which had previously been cut with SalI and ligated to the same oligonucleotide pair. This vector is designated as sfHAV-EO410. DNA was electroporated (Dower et al., *Nucleic Acids Res.*, 16:6127–6145, (1988) into *E. coli* DH10B, and after one hour growth at 37° C., the transformed cells were frozen in one milliliter aliquots in SOC medium (Hanahan et al., *J. Mol. Biol.*, 166:557–580, (1983) containing 20% glycerol. One aliquot was titered to determine the number of ampicillin-resistant colonies. The resulting 0.3A4 library had 1.84 million clones.

*E. coli* strain DH10B cells transfected with the cDNA library in sfHAV-EO410 were plated to provide approximately 1600 colonies per plate. Colonies were scraped from each plate, pooled, and plasmid DNA prepared from each pool. The pooled DNA, representing about 1600 colonies, was then used to transfect a sub-confluent layer of CV-1/EBNA-1 cells using DEAE-dextran followed by chloroquine treatment, similar to that described by Luthman et al., *Nucl. Acids Res.* 11:1295, (1983) and McCutchan et al., *J. Natl. Cancer Inst.* 41:351, (1986). The CV-1/EBNA-1 cell line (ATCC CRL10478) constitutively expresses EBV nuclear antigen-1 driven from the CMV immediate-early enhancer/promoter. CV1-EBNA-1 was derived from the African Green Monkey kidney cell line CV-1 (ATCC CCL 70), as described by McMahan et al. (*EMBO J.* 10:2821, 1991).

In order to transfect the CV-1/EBNA-1 cells with the cDNA library, the cells were maintained in complete medium (Dulbecco's modified Eagle's media (DMEM) containing 10% (v/v) fetal calf serum (FCS), 50 U/ml penicillin, 50 U/ml streptomycin, 2 mM L-glutamine) and were plated at a density of about $2 \times 10^5$ cells/well on single-well chambered slides (Lab-Tek). Slides were pretreated with 1 ml human fibronectin (10 µg/ml in PBS) for 30 minutes followed by 1 wash with PBS. Media was removed from the adherent cell layer and replaced with 1.5 ml complete medium containing 66.6 µM chloroquine sulfate. Two-tenths ml of DNA solution (2 µg DNA, 0.5 mg/ml DEAE-dextran in complete medium containing chloroquine) was then added to the cells and incubated for 5 hours. Following the incubation, the media was removed and the cells shocked by addition of complete medium containing 10% DMSO for 2.5 to 20 minutes followed by replacement of the solution with fresh complete medium. The cells were cultured for 2 to 3 days to permit transient expression of the inserted sequences.

Transfected monolayers of CV-1/EBNA-1 cells were assayed for expression of flt3-L by slide autoradiography essentially as described by Gearing et al. (*EMBO J.* 8:3667, 1989). Transfected CV-1/EBNA-1 cells (adhered to chambered slides) were washed once with binding medium with nonfat dry milk (BM-NFDM) (RPMI medium 1640 containing 25 mg/ml bovine serum albumin (BSA), 2 mg/ml sodium azide, 20 mM HEPES, pH 7.2, and 50 mg/ml nonfat dry milk). Cells were then incubated with flt3:Fc in BM-NFDM (1 µg/ml) for 1 hour at room temperature. After incubation, the cell monolayers in the chambered slides were washed three times with BM-NFDM to remove unbound flt3:Fc fusion protein and then incubated with 40 ng/ml $^{125}$I-mouse anti-human Fc antibody (described below) (a 1:50 dilution) for 1 hour at room temperature. The cells were washed three times with BM-NFDM, followed by 2 washes with phosphate-buffered saline (PBS) to remove unbound $^{125}$I-mouse anti-human Fc antibody. The cells were fixed by incubating for 30 minutes at room temperature in 2.5% glutaraldehyde in PBS, pH 7.3, washed twice in PBS and air dried. The chamber slides containing the cells were exposed on a Phophorimager (Molecular Dynamics) overnight, then dipped in Kodak GTNB-2 photographic emulsion (6× dilution in water) and exposed in the dark for 3–5 days at 4° C. in a light proof box. The slides were then developed for approximately 4 minutes in Kodak D19 developer (40 g/500 ml water), rinsed in water and fixed in Agfa G433C fixer. The slides were individually examined with a microscope at 25–40× magnification and positive cells expressing flt3-L were identified by the presence of autoradiographic silver grains against a light background.

The mouse anti-human Fc antibody was obtained from Jackson Laboratories. This antibody showed minimal binding to Fc proteins bound to the Fcγ receptor. The antibody was labeled using the Chloramine T method. Briefly, a Sephadex G-25 column was prepared according to the manufacturer's instructions. The column was pretreated with 10 column volumes of PBS containing 1% bovine serum albumin to reduce nonspecific adsorption of antibody to the column and resin. Nonbound bovine serum albumin was then washed from the column with 5 volumes of PBS lacking bovine serum albumin. In a microfuge tube 10 µg of antibody (dissolved in 10 µl of PBS) was added to 50 µl of 50 mM sodium phosphate buffer (pH 7.2) 2.0 mCi of carrier-free Na$^{125}$I was added and the solution was mixed well. 15 µl of a freshly prepared solution of chloramine-T (2 mg/ml in 0.1 M sodium phosphate buffer (pH 7.2)) was then added and the mixture was incubated for 30 minutes at room temperature, and the mixture then was immediately applied to the column of Sephadex G-25. The radiolabelled antibody was then eluted from the column by collecting 100–150 µl fractions of eluate. Bovine serum albumin was added to the eluted fractions containing the radiolabeled antibody to a final concentration of 1%. Radioiodination yielded specific activities in the range of $5-10 \times 10^{15}$ cpm/nmol protein.

Using the slide autoradiography approach, the approximately 1,840,000 cDNAs were screened in pools of approximately 1,600 cDNAs until assay of one transfectant pool showed multiple cells clearly positive for flt3:Fc binding. This pool was then partitioned into pools of 500 and again screened by slide autoradiography and a positive pool was identified. This pool was partitioned into pools of 100 and again screened. Individual colonies from this pool of 100 were screened until a clone (clone #6C) was identified which directed synthesis of a surface protein with detectable flt3:Fc binding activity. This clone was isolated, and its 0.88 kb cDNA insert was sequenced.

The nucleotide and encoded amino acid sequences of the coding region of the murine flt3-ligand cDNA of clone #6C are presented in SEQ ID NOs:1 and 2. The cDNA insert is 0.88 kb in length. The open-reading frame within this sequence could encode a protein of 231 amino acids. Thus, DNA and encoded amino acid sequences for the 231-amino acid open reading frame are presented in SEQ ID NOs:1 and 2. The protein of SEQ ID NO:2 is a type I transmembrane protein, with an N-terminal signal peptide (amino acids 1 to 27), an extracellular domain (amino acids 28–188) a transmembrane domain (amino acids 189–211) and a cytoplasmic domain (amino acids 212–231). The predicted molecular weight of the native protein following cleavage of the signal sequence is 23,164 daltons. The mature protein has an estimated pI of 9.372. There are 56 bp of 5' noncoding sequence and 126 bp of 3' non-coding sequence flanking the coding region, including the added cDNA adapters. The above-described cloning procedure also produced a murine flt3 ligand clone #5H, which is identical to the #6C clone beginning at nucleotide 49 and continuing through nucleotide 545 (corresponding to amino acid 163) of SEQ ID NO:1. The #5H clone completely differs from that point onward, and represents an alternate splicing construct.

The vector sfHAV-EO410 containing the flt3-L cDNA in *E. coli* DH10B cells was deposited with the American Type Culture Collection, Rockville, Md., USA (ATCC) on Apr. 20, 1993 and assigned accession number ATCC 69286. The deposit was made under the terms of the Budapest Treaty.

EXAMPLE 4

Cloning of cDNA Encoding Human Flt3-L

A cDNA encoding human flt3-L was cloned from a human clone 22 T cell λgt10 random primed cDNA library as described by Sims et al., *PNAS*, 86:8946–8950 (1989). The library was screened with a 413 bp Ple I fragment corresponding to the extracellular domain of the murine flt3-L (nucleotides 103–516 of SEQ ID NO:1). The fragment was random primed, hybridized overnight to the library filters at 55° C. in oligo prehybridization buffer. The fragment was then washed at 55° C. at 2×SSC/0.1% SDS for one hour, followed by 1×SSC/0.1% SDS for one hour and then by 0.5×SSC/0.1% SDS for one hour. The DNA from the positive phage plaques was extracted, and the inserts were amplified by PCR using oligonucleotides specific for the phage arms. The DNA was then sequenced, and the sequence for clone #9 is shown in SEQ ID NO:5. Additional human flt3-L cDNA was isolated from the same λgt10 random primed cDNA library as described above by screening the library with a fragment of the extracellular domain of the murine clone #5H cDNA comprising a cDNA sequence essentially corresponding to nucleotides 128–541 of SEQ ID NO:1.

Sequencing of the 988 bp cDNA clone #9 revealed an open reading frame of 705 bp surrounded by 29 bp of 5' non-coding sequence and 250 bp of 3' non-coding sequence. The 3' non-coding region did not contain a poly-A tail. There were no in-frame stop codons upstream of the initiator methionine. The open reading frame encodes a type I transmembrane protein of 235 amino acids as shown by amino acids 1–235 of SEQ ID NO:6. The protein has an N-terminal signal peptide of alternatively 26 or 27 amino acids. There exists a slightly greater probability that the N-terminal signal peptide is 26 amino acids in length than 27 amino acids in length. The signal peptide is followed by a 156 or a 155 amino acid extracellular domain (for signal peptides of 26 and 27 amino acids, respectively); a 23 amino acid transmembrane domain and a 30 amino acid cytoplasmic domain. Human flt3-L shares overall 72% amino acid identity and 78% amino acid similarity with murine flt3-L. The vector pBLUESCRIPT SK(−) containing the human flt3-L cDNA of clone #9 was deposited with the American Type Culture Collection, Rockville, Md., USA (ATCC) on Aug. 6, 1993 and assigned accession number ATCC 69382. The deposit was made under the terms of the Budapest Treaty.

EXAMPLE 5

Expression of Flt3-L in Yeast

For expression of soluble flt3-L in yeast, synthetic oligonucleotide primers were used to amplify via PCR (Mullis and Faloona, *Meth. Enzymol.* 155:335–350, 1987) the entire extracellular coding domain of flt3-L between the end of the signal peptide and the start of the transmembrane segment. The 5' primer (5'-AATTGGTACCTTGGATAAAA-GAGACTACAAGGACGACGATGACAAGA-CACCTGACTGTTACTACTTCAGCCAC-3') SEQ ID NO:7 encoded a portion of of the alpha factor leader and an antigenic octapeptide, the FLAG sequence fused in-frame with the predicted mature N-terminus of flt3-L. The 3' oligonucleotide (5'-ATATGGATCCCTACTGCCTGGGC-CGAGGCTCTGGGAG-3') SEQ ID NO:8 created a termination codon following Gln-189, just at the putative transmembrane region. The PCR-generated DNA fragment was ligated into a yeast expression vector (for expression in *K. lactis*) that directs secretion of the recombinant product into the yeast medium (Fleer et. al., *Gene*, 107:285–195 (1991); and van den Berg et. al., *Bio/Technology*, 8:135–139 (1990)). The FLAG:flt3-L fusion protein was purified from yeast broth by affinity chromatography as previously described (Hopp et. al., *Biotechnology*, 6:1204–1210, 1988).

EXAMPLE 6

Monoclonal Antibodies to Flt3-L

This example illustrates a method for preparing monoclonal antibodies to flt3-L. Flt3-L is expressed in mammalian host cells such as COS-7 or CV-1/EBNA-1 cells and purified using flt3:Fc affinity chromatography. Purified flt3-L, a fragment thereof such as the extracellular domain, synthetic peptides or cells that express flt3-L can be used to generate monoclonal antibodies against flt3-L using conventional techniques, for example, those techniques described in U.S. Pat. No. 4,411,993. Briefly, mice are immunized with flt3-L as an immunogen emulsified in complete Freund's adjuvant, and injected in amounts ranging from 10–100 μg subcutaneously or intraperitoneally. Ten to twelve days later, the immunized animals are boosted with additional flt3-L emulsified in incomplete Freund's adjuvant. Mice are periodically boosted thereafter on a weekly to bi-weekly immunization schedule. Serum samples are periodically taken by retro-orbital bleeding or tail-tip excision to test for flt3-L antibodies by dot blot assay, ELISA (Enzyme-Linked Immunosorbent Assay) or inhibition of flt3 binding.

Following detection of an appropriate antibody titer, positive animals are provided one last intravenous injection of flt3-L in saline. Three to four days later, the animals are sacrificed, spleen cells harvested, and spleen cells are fused to a murine myeloma cell line, e.g., NS1 or preferably P3×63Ag8.653 (ATCC CRL 1580). Fusions generate hybridoma cells, which are plated in multiple microtiter plates in a HAT (hypoxanthine, aminopterin and thymidine) selective medium to inhibit proliferation of non-fused cells, myeloma hybrids, and spleen cell hybrids.

The hybridoma cells are screened by ELISA for reactivity against purified flt3-L by adaptations of the techniques disclosed in Engvall et al., *Immunochem.* 8:871, 1971 and in U.S. Pat. No. 4,703,004. A preferred screening technique is the antibody capture technique described in Beckmann et al., (*J. Immunol.* 144:4212, 1990) Positive hybridoma cells can be injected intraperitoneally into syngeneic BALB/c mice to produce ascites containing high concentrations of anti-flt3-L monoclonal antibodies. Alternatively, hybridoma cells can be grown in vitro in flasks or roller bottles by various techniques. Monoclonal antibodies produced in mouse ascites can be purified by ammonium sulfate precipitation, followed by gel exclusion chromatography. Alternatively, affinity chromatography based upon binding of antibody to protein A or protein G can also be used, as can affinity chromatography based upon binding to flt3-L.

What is claimed is:

1. An antibody that binds to mouse flt-3 ligand encoded by the cDNA insert in vector sfHAV-EO410 in *E. coli* DH10B cells having ATCC Accession No. 69286.

2. An antibody that binds to mouse flt-3 ligand, wherein said mouse flt-3 ligand comprises amino acids 28–163 of SEQ ID NO:2.

3. The antibody of claim 2, wherein said mouse flt-3 ligand comprises amino acids 28–188 of SEQ ID NO:2.

4. The antibody of claim 2, wherein said mouse flt-3 ligand comprises amino acids 1–188 of SEQ ID NO:2.

5. The antibody of claim 2, wherein said mouse flt-3 ligand comprises amino acids 1–231 of SEQ ID NO:2.

6. The antibody of claim 1, wherein said antibody is a monoclonal antibody.

7. The antibody of claim 2, wherein said antibody is a monoclonal antibody.

8. The antibody of claim 3, wherein said antibody is a monoclonal antibody.

9. The antibody of claim 4, wherein said antibody is a monoclonal antibody.

10. The antibody of claim 5, wherein said antibody is a monoclonal antibody.

11. A pharmaceutical composition comprising the antibody of claim 1; and a pharmaceutically acceptable carrier.

12. A pharmaceutical composition comprising the antibody of claim 2; and a pharmaceutically acceptable carrier.

13. A pharmaceutical composition comprising the antibody of claim 3; and a pharmaceutically acceptable carrier.

14. A pharmaceutical composition comprising the antibody of claim 4; and a pharmaceutically acceptable carrier.

15. A pharmaceutical composition comprising the antibody of claim 5; and a pharmaceutically acceptable carrier.

* * * * *